US008790629B2

(12) United States Patent
Cao et al.

(10) Patent No.: US 8,790,629 B2
(45) Date of Patent: *Jul. 29, 2014

(54) HIGH VISCOSITY HEAT-TREATED XANTHAN GUM

(71) Applicant: Akzo Nobel N.V., Arnhem (NL)

(72) Inventors: Hongjie Cao, Hillsborough, NJ (US); Gary T. Martino, Monmouth Junction, NJ (US)

(73) Assignee: Akzo Nobel N. V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/972,237

(22) Filed: Aug. 21, 2013

(65) Prior Publication Data

US 2013/0336907 A1    Dec. 19, 2013

Related U.S. Application Data

(62) Division of application No. 10/371,459, filed on Feb. 21, 2003, now Pat. No. 8,545,828.

(51) Int. Cl.
| A61K 8/73 | (2006.01) |
| A61Q 5/02 | (2006.01) |
| A61Q 5/04 | (2006.01) |
| A61Q 5/06 | (2006.01) |
| A61Q 5/10 | (2006.01) |
| A61Q 5/12 | (2006.01) |
| A61Q 19/00 | (2006.01) |
| A61Q 1/02 | (2006.01) |
| A61Q 19/10 | (2006.01) |
| A61Q 17/04 | (2006.01) |

(52) U.S. Cl.
USPC .......... 424/70.13; 424/401; 424/59; 510/119; 510/130

(58) Field of Classification Search
CPC ...... A61K 2800/10; A61K 8/73; A61Q 17/04; A61Q 19/00; A61Q 19/10; A61Q 1/02; A61Q 5/02; A61Q 5/04; A61Q 5/06; A61Q 5/10; A61Q 5/12
See application file for complete search history.

(56) References Cited

U.S. PATENT DOCUMENTS

| 3,349,077 | A | 10/1967 | Schweiger |
| 4,209,729 | A | 6/1980 | McElroy |
| 4,465,702 | A | 8/1984 | Eastman et al. |
| 4,477,480 | A | 10/1984 | Seidel et al. |
| 4,591,610 | A | 5/1986 | Grollier |
| 4,595,586 | A | 6/1986 | Flom |
| 4,667,026 | A | 5/1987 | Jarry et al. |
| 4,874,854 | A | 10/1989 | Colegrove et al. |
| 5,037,929 | A | 8/1991 | Rajagopalan et al. |
| 5,131,953 | A | 7/1992 | Kasica et al. |
| 5,149,799 | A | 9/1992 | Rubens |
| 5,187,272 | A | 2/1993 | Katcher et al. |
| 5,198,469 | A | 3/1993 | Sakata |
| 5,206,009 | A | 4/1993 | Watling et al. |
| 5,508,055 | A | 4/1996 | Rubow et al. |
| 5,538,720 | A | 7/1996 | Jendryssek-Pfaff et al. |
| 5,593,503 | A | 1/1997 | Shi et al. |
| 5,679,556 | A | 10/1997 | Homma et al. |
| 5,753,215 | A | 5/1998 | Mougin et al. |
| 5,879,669 | A | 3/1999 | Clausen et al. |
| 6,017,860 | A | 1/2000 | Sajic et al. |
| 6,090,375 | A | 7/2000 | Rechelbacher et al. |
| 6,113,881 | A | 9/2000 | Bhatt et al. |
| 6,147,038 | A | 11/2000 | Halloran |
| 6,180,122 | B1 | 1/2001 | Roulier et al. |
| 6,218,346 | B1 | 4/2001 | Sajic et al. |
| 6,531,118 | B1 | 3/2003 | Gonzalez et al. |
| 6,716,418 | B2 | 4/2004 | Sengupta et al. |
| 6,887,400 | B1 | 5/2005 | Wei et al. |
| 7,014,842 | B2 | 3/2006 | Dueva-Koganov et al. |
| 2003/0049290 | A1 | 3/2003 | Jha et al. |
| 2003/0108505 | A1 | 6/2003 | Cao et al. |
| 2003/0143179 | A1 | 7/2003 | Cao et al. |
| 2003/0228267 | A1 | 12/2003 | Aust et al. |
| 2004/0234486 | A1 | 11/2004 | Hashimoto |

FOREIGN PATENT DOCUMENTS

| EP | 0 180 366 A2 | 5/1986 |
| EP | 0 321 216 A2 | 6/1989 |
| EP | 0 412 705 A2 | 2/1991 |
| EP | 0 554 818 A2 | 8/1993 |
| EP | 0 664 113 A2 | 7/1995 |
| EP | 0 784 970 A2 | 7/1997 |
| EP | 0 823 252 A2 | 2/1998 |
| EP | 0 911 345 A2 | 4/1999 |
| EP | 1 166 767 A2 | 1/2002 |
| FR | 2 606 423 A1 | 5/1988 |
| GB | 2 331 302 A | 5/1999 |
| GB | 2 380 938 A | 4/2003 |
| JP | 62-263111 A | 11/1987 |

(Continued)

OTHER PUBLICATIONS

Merriam-Webster Dictionary, "Ash—Definition," http://www.merriam-webster.com/dictionary/ash?show=1&t=1286216645, Oct. 4, 2010.

(Continued)

Primary Examiner — Rachael E Bredefeld
(74) Attorney, Agent, or Firm — Norris McLaughlin & Marcus, P.A.

(57) ABSTRACT

The present invention is directed to heat treated xanthan gums, which have improved solution viscosity over other xanthan gums heat-treated under the same processing conditions while maintaining the improved ease of use and the short, non-stringy gel texture of heat treated xanthan gums. Such high solution viscosity xanthan gums are suitable in a variety of applications, including cosmetic and personal care compositions.

10 Claims, No Drawings

(56) References Cited

FOREIGN PATENT DOCUMENTS

| | | |
|---|---|---|
| JP | 63-150215 A | 6/1988 |
| JP | 05-221838 A | 8/1993 |
| JP | 07-061910 A | 3/1995 |
| JP | 07-69838 A | 3/1995 |
| JP | 07-233034 | 9/1995 |
| JP | 8-193055 | 7/1996 |
| JP | 08-231354 A | 9/1996 |
| JP | 09-255534 A | 9/1997 |
| JP | 10-33125 | 2/1998 |
| JP | 10-067630 | 3/1998 |
| JP | 11-236310 | 8/1999 |
| JP | 2000-53552 A | 2/2000 |
| JP | 2004-339108 A | 12/2004 |
| WO | WO 95/04082 A2 | 2/1995 |
| WO | WO 97/46606 A1 | 12/1997 |
| WO | WO 98/09608 A2 | 3/1998 |
| WO | WO 99/15135 A1 | 4/1999 |
| WO | WO 01/96461 A1 | 12/2001 |

OTHER PUBLICATIONS

Chinese Office Action for corresponding Chinese Application No. 2008-019104 dated Apr. 30, 2013.

Torres, L.G., et al.; "Apparent Yield Stress of Xanthan Solutions and Broths"; Bioprocess Engineering, vol. 12, pp. 41-46, 1995.

"Vanzan Xanthan Gum", Vanderbilt Report No. 916, R.T. Vanderbilt Company, Inc., Norwalk, Connecticut, pp. 1-8, published prior to Feb. 21, 2003.

Wurzburg, O.B.; "Modified Starches: Properties and Uses"; CRC Press, Inc., Boca Raton, Florida, 1986, entire book.

Powell, Eugene L.; "Production & Use of Pregelatinized Starch," Starch Chemistry & Technology, vol. III—Industrial Aspects, Chpt. XXII, pp. 523-536; Academic Press; New York; 1967.

National Starch Personal Care Sunscreen Formulation, "Facial Clear Sunscreen Gel SPF 30-Water Resistant 11716-6-7," www.personalcarepolymers.com, published Mar. 31, 2004.

French Search Report of corresponding FR Application No. 0210368000 dated Aug. 19, 2005.

Fitzpatrick, "Xanthan Gum—The Natural Water for Cosmetic and Personal Care Products", In-Cosmetics; London, UK; vol. 2; pp. 37-40; Mar. 1993.

HIGH VISCOSITY HEAT-TREATED XANTHAN GUM

The present application is a divisional of U.S. patent application Ser. No. 10/371,459, filed on Feb. 21, 2003.

BACKGROUND OF THE INVENTION

The present invention relates to a high viscosity xanthan gum formed by heat treatment and compositions comprising such xanthan gum.

Xanthan gum is a polysaccharide gum derived from the bacterium *Xanthomonas* and is well known in the art. It is composed of a main chain comprising β-(1,4) D-glucose units. Trisaccharide side chains on alternating anhydroglucose units are composed of a glucuronic acid residue between two mannose units. At most of the terminal mannose units is a pyruvate moiety and the non-terminal mannose carries an acetyl group. It has pseudoplastic or shear-thinning behavior characterized by a decrease in apparent viscosity in response to an increase in shear rate.

Xanthan gum is typically used in many industrial applications as a rheology modifier; thickening, viscosifying and gelling when combined with other polymers. It has also been used to impart stability to emulsions and prevent the settling out of solids. Its limited ability to disperse in either hot or cold water allows xanthan gum to be formulated into a broad variety of applications including pharmaceuticals, household products, foods, and personal care products.

Xanthan gum is widely used in cosmetics and personal care industry as a rheology control agent for aqueous systems. However, currently available xanthan gums need to be improved to enhance its properties, broaden its applications, and provide functionality at a lower cost.

Xanthan gum with an apparent average molecular weight of greater than 16,000,000 has been used to stabilize and improve the feel of emulsified cosmetics such as toilet water, creams and cleansing gels (JP Application No. 10-140503).

Xanthan gum which has been heat-treated is also known in the art. For example, EP 321 216 enhances the viscosity profile of xanthan gum by thermally treating it in the dry state (15% moisture or less). Heat treatment of xanthan gum is also known in JP Application No. 8-193055 which heat treats xanthan gum in the powdered form.

Surprisingly, it has now been discovered that certain heat treated xanthan gums have superior solution viscosity and thickening efficiency while maintaining the improved ease of use and the short, non-stringy gel texture of heat treated xanthan gums. Such high solution viscosity xanthan gums are suitable in a variety of applications, including cosmetic and personal care compositions.

SUMMARY OF THE INVENTION

The present invention is directed to heat treated xanthan gums, which have improved solution viscosity over other xanthan gums under the same processing (heat-treatment) conditions while maintaining the improved ease of use and the short, non-stringy gel texture of heat treated xanthan gums. Such high solution viscosity xanthan gums are suitable in a variety of applications, including cosmetic and personal care compositions.

Solution viscosity, as used herein, means the viscosity of xanthan gum at 1% in an aqueous solution as measured using a Brookfield DV-I viscometer with a Spindle #6 at 10 rpm.

DETAILED DESCRIPTION OF THE INVENTION

The present invention is directed to heat treated xanthan gums, which have improved solution viscosity over other xanthan gums xanthan gums under the same processing (heat-treatment) conditions while maintaining the improved ease of use and the short, non-stringy gel texture of heat treated xanthan gums. Such high solution viscosity xanthan gums are suitable in a variety of applications, including cosmetic and personal care compositions.

Any xanthan gum which results in the improved solution viscosity of the present invention may be used as a starting material. Particularly useful xanthan gums are those having an ash content (after 18 hours at 650 degc) of less than about 8.5%, and an aqueous solution viscosity of more than 3000 cps at a level of 1% solids (wt/wt). Such xanthan gums are commercially available, for example from Archer Daniel Midland.

Heat treatment of xanthan gum is typically done at low moisture, particularly less than about 25%, more particularly less than about 8%, most particularly less than about 1%, at a temperature of at least about 60° C., more particularly at least 100° C., and most particularly at least about 105° C. for a period of time of about 30 minutes, particularly at least one hour, more particularly at least 2 hours. Typically, the temperature is less than about 120° C. for a period of less than about 4 hours.

The moisture content, pH, temperature and time of heat treatment may be adjusted by one skilled in the art to achieve the viscosity, dispersibility, gel texture, solution clarity, and other properties desired. It will further be dependent upon the starting material used (grade, viscosity, molecular weight, and particle size). Typically, low moisture is used to improve the impact of heat-treatment. However, at any given moisture, increasing the temperature or time generally increases viscosity to a maximum and further heating decreases the viscosity of the xanthan gum at the concentrations used in this invention. Acidic pHs are typically more suitable; a pH of 2-4 is most suitable.

Heat treatment of xanthan gum may be accomplished by a variety of methods known in the art including without limitation oven, fluidized bed, infrared and microwave heat treatments. The particle size of the resultant heat-treated xanthan gum may be adjusted using methods known in the art such as milling.

The xanthan gum may further be modified either before or after heat treatment. The xanthan gum may be converted by oxidation, enzyme conversion, acid hydrolysis, heat and/or acid dextrinization, or shear. The xanthan gum may also be chemically, enzymatically or physically modified. Suitable chemical derivatives include esters, such as the acetate, and half esters, such as the succinate, octenyl succinate and tetradecenyl succinate; phosphate derivatives; ethers such as hydroxyalkyl ethers and cationic ethers; or any other derivatives or combinations thereof. Modification may also be by chemical crosslinking. Crosslinking agents suitable for use herein include phosphorus oxychloride, epichlorohydrin, sodium trimetaphosphate and adipic-acetic mixed acid anyhrides. Such processes are also known in the art.

The xanthan gum may also be purified by any method known in the art to remove off flavors, colors, and contaminants that are native to the xanthan gum or are created during the modification or heat treatment processes as long as the heat treatment is not substantially impacted.

The heat treated xanthan gums of the present invention differ in that they have an increased solution viscosity (at 1% solids in an aqueous solution) of at least about 12,500 cps, particularly at least about 15,000 cps. In particular, the solution viscosity increases at least about 10,000 cps, particularly at least about 15,000 cps, over the viscosity prior to treatment, depending upon the heat treatment conditions used. Further, the solution viscosity increase at least about 150%, more particularly at least about 200% over that of similarly treated xanthan gums which are not suitable for this invention.

The resultant heat-treated xanthan gum typically has improved dispersibility, such that under given conditions of temperature and agitation, the time to fully disperse the resultant gum is typically reduced by 25%, more particularly 50%, most particularly 70% compared to non-heat treated xanthan. It also generally provides improved thickening ability, rheology modification, emulsion stabilization, suspending ability, texture enhancement, film forming and foam stabilization.

Heat treated xanthan gum provides clear to translucent clarity and is easy to use as it is dispersible in either hot or cold water and needs no neutralization. It exhibits tolerance to salt and extreme pH, particularly in the range of about 2 to about 12, is biodegradable, and may be labeled as natural.

The heat modification of xanthan gum improves the ease of use, including the ease of dispersing in solution with less tendency to form fish eyes. Heat modification also not only improves the thickening efficiency, but also the gel texture, reducing the stringiness or pituitousness of the long texture. In addition, heat treatment of xanthan increases its viscosity in a variety of pH and salt ranges. Heat treated xanthan gum is compatible with anionic, cationic or nonionic polymers, allowing it to be formulated with a variety of commonly used additives.

Heat-treated xanthan gum may be used in a variety of compositions, including without limitation, cosmetic and personal care compositions, detergents and household cleaning compositions, paper products, oil field chemicals, and food and beverage compositions. Cosmetic and personal care compositions include skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with AHA and BHA and hair fixatives such as sprays, gels, mousses, pomades, and waxes, including low VOC hair fixatives. The compositions may be in any form, including without limitation, emulsions, gels, liquids, sprays, solids, mousses, powders, wipes, or sticks.

Heat treated xanthan gum may be formulated into compositions at any level which provides the desired properties. Typically, less heat-treated xanthan gum will be needed to achieve the same properties and functionality as native xanthan gum. The heat-treated xanthan gums will typically be used in an amount of at least about 0.01%, particularly at least about 0.5%, more particularly at least about 0.75% and less than about 20%, particularly less than about 2%, more particularly less than about 1.5%. The amount used will depend not only upon the properties desired, but also upon the heat treatment levels and other ingredients.

The heat-treated xanthan gum may be incorporated into the composition in the same manner as native xanthan gum. For example, the heat-treated xanthan gum may be dispersed in water and then the remaining components may be added.

EXAMPLES

The following examples are presented to further illustrate and explain the present invention and should not be taken as limiting in any regard. All percents used are on a weight/weight basis.

The following procedures were used throughout the examples.

Viscosity—Viscosity is measured using a Brookfield DV-I viscometer with a Spindle #6 at 10 rpm.

Crossover Strain—Crossover strain, as used herein, is measured using a controlled stress or strain rheometer at a frequency of 1 rad/s and 25° C. The tangent of the phase angle, tangent of delta (tandelta) is plotted versus the strain amplitude and the crossover strain is that at which the tandelta is equal to one.

Ash Content—Samples were ashed by placing 4 grams of a sample at 650° C. for 18 hours and weighing. Percent ash was determined by dividing the weight of the sample after ashing by the initial sample weight.

The following raw materials were used in the examples and are defined as follows:

ADM=xanthan gum commercially available from Archer Daniel Midland, Decatur, Ill., available as NF/FCC 80 Mesh Transparent Food Grade Keltrol T=xanthan gum from CP Kelco, Chicago, Ill.

Example 1

Preparation of Oven Heat-Treated Xanthan Gums and Comparison Thereof

Several xanthan gum samples with varying 1% aqueous solution viscosity and percent ash content were heat-treated by heating 10 grams of xanthan gum powder in a vented oven at 110° C. for 180 minutes. The results are shown in Table I.

TABLE I

Viscosity comparison of different xanthan gums.

| Xanthan Gum Samples | Solution Viscosity (cps) | | Viscosity Change | Ash (%) |
|---|---|---|---|---|
| | Before Heat-Treatment | After Heat-Treatment | | |
| J-1 | 3700 | 9700 | 6000 | 10.1 |
| J-2 | 2500 | 6800 | 4300 | 8.8 |
| J-3 | 2200 | 10500 | 8300 | 8.4 |
| A-1 | 3600 | 27800 | 24200 | 7.4 |
| A-2 | 3900 | 15500 | 11600 | 7.8 |
| A-3 | 3200 | 18500 | 15300 | 7.2 |
| K-1 | 2100 | 9000 | 6900 | 8.7 |
| K-2 | 1900 | 7700 | 5800 | 8.5 |
| K-3 | 2600 | 10800 | 8200 | 8.4 |

Example 2

Preparation of Fluid Bed Heat-Treated Xanthan Gums and Comparison Thereof

Several xanthan gum samples with varying 1% aqueous solution viscosity and percent ash content were heat-treated by heating the xanthan gum powder in a fluid bed dryer at 220° F. (104° C.) for 180 minutes. After heat-treatment, 1 percent solutions were made of the xanthan gum samples, and their viscosity measured two days later. The results are listed in Table II.

TABLE II

Comparison of xanthan gum heat-treated in a fluid bed dryer.

| Untreated Xanthan Gum Samples | Solution Viscosity (cps) | | | |
|---|---|---|---|---|
| | Before Heat-Treatment | After Heat-Treatment | Viscosity Change | Ash |
| A-1 | 3600 | 35,600 | 32000 | 7.4 |
| J-3 | 2200 | 15,500 | 13300 | 8.4 |
| K-1 | 2100 | 18,400 | 16300 | 8.7 |

As can be seen from the above table, the viscosity of the heat-treated xanthan made with xanthan having an initial ash content of less than 8.5% and a 1% aqueous solution viscosity of more than 3000 cps, is much higher than that using other xanthan gums.

Example 3

Preparation of a 6% VOC Mousse with Heat-Treated Xanthan Gum

| Ingredients | % w/w | % w/w | % w/w |
|---|---|---|---|
| Heat-treated Xanthan gum[1] | 0.6 | 0.6 | 0.6 |
| Propylene Glycol | 1.0 | 1.0 | 1.0 |
| Brij 30[2] | 0.4 | 0.2 | — |
| DC 193[3] | 0.2 | 0.2 | 0.2 |
| Dowicil 200[4] | 0.2 | 0.2 | 0.2 |
| Deionized Water | 91.6 | 91.8 | 92.0 |
| Propellant A-46[5] | 6.0 | 6.0 | 6.0 |
| | 100 | 100 | 100 |

[1]Heat-treated ADM xanthan gum (Fluid bed reactor at 220° F. for 180 minutes)
[2]Laureth-4 (Uniqema)
[3]Dimethicone Copolyol (Dow Corning)
[4]Quaternium-15 (Dow Chemical Co.)
[5]Isobutane/Propane Heat-treated xanthan gum is suited for use in any type of styling mousses, including 6% VOC mousses and surfactant-free mousses. In addition to providing hold to the mousses, heat-treated xanthan gum contributes to the conditioning and non-tacky feel.

Example 4

Skin Gel

| Ingredients | % w/w |
|---|---|
| Part A | |
| Heat-treated xanthan gum[1] | 1.0 |
| D.I. Water | 96.92 |
| Preservative | q.s. |
| Part B | |
| Glycerin | 2.0 |
| Highly Reflective Mirror Glitter[2] | 0.1 |
| PEG-40 Hydrogenated Castor Oil[3] | 0.06 |
| Fragrance | 0.02 |

[1]Fluid bed heat treated at 225° F. for 2.5 hr
[2]Visible Mirror(3M)
[3]Cremophor RH 40 (BASF)

Xanthan gum is used in this skin gel formulation as a thickening and suspending agent. Xanthan gum provides a gel matrix and a film that resists rub-off of the glitters, and offers a smooth and soft skin feel. Combining with glycerin, it may also moisturize the skin.

Example 5

Skin Toner/Serum

| Ingredients | % w/w |
|---|---|
| Part A | |
| Xanthan gum[1] | 0.5 |
| D.I. Water | 77.5 |
| Preservative | q.s. |
| Part B | |
| Glycerin | 2.0 |
| Distilled Witch hazel[2] (14% alcohol extract) | 20.0 |

[1]Fluid bed heat treated at 225° F. for 2.5 hr
[2]*Hamamelis virginiana* (American Distilling)

Xanthan gum is used in this formula as a thickener, a film form, and a skin feel enhancer. The film formed by xanthan gum on the skin may help to improve the skin tone/skin firmness.

Example 6

Skin Care Emulsion

| Ingredients | % w/w |
|---|---|
| Part A | |
| Glycerin monostearate[1] | 0.95 |
| Stearic acid | 1.9 |
| C12-15 Alkyl Benzoate[2] | 2.5 |
| Caprilic/Capric Triglyceride[3] | 3.0 |
| Isopropyl Myristate | 2.5 |
| Jojoba oil | 2.0 |
| Part B | |
| Triethanolamine | 0.35 |
| Propylene glycol | 3.0 |
| Deionized water | 41.35 |
| Part C | |
| Xanthan gum[4] | 0.6 |
| Deionized water | 40.85 |
| Preservative | q.s. |

[1]Tegin M (Glodschmidt)
[2]Finsolv TN (Fintex)
[3]Miglycol 812 (Huls AG/Huls America)
[4]Fluid bed heat treated at 225° F. for 2.5 hr Xanthan gum is used to improve emulsion stability, and to efficiently thicken the system. It imparts nice skin after feel to the product.

Example 7

Cream Foundation with Xanthan Gum

| Ingredients | % w/w |
|---|---|
| Part A | |
| D.I. Water | q.s. |
| PEG-8 [1] | 5.0 |
| Propylene glycol | 5.0 |
| Xanthan gum [2] | 0.6 |
| Part B | |
| Decyl oleate [3] | 2.2 |
| Glyceryl monostearate SE [4] | 0.9 |
| Sorbitan stearate | 1.5 |
| Stearyl alcohol | 0.5 |
| Part C | |
| Iron oxide | 2.0 |
| Titanium dioxide | 6.0 |
| Kaolin | 7.0 |
| Part D | |
| Cyclomethicone [5] | 15.0 |
| Part E | |
| Preservative | q.s. |

[1] POLYGLYCOL E-400 (Dow Corning)
[2] Fluid bed heat treated at 225° F. for 2.5 hr
[3] CERAPHYL 140A (ISP Van Dyk)
[4] CERASYNT Q (ISP Van Dyk)
[5] DC 344 (Dow Corning)

Xanthan gum is used in this formula as a rheology modifier, emulsion stabilizer, film former, feel enhancer, and a suspending agent. It may help to provide a product with enhanced stability and nice and smooth skin feel.

Example 8

Xanthan Gum in Body Wash/Liquid Soap

| Ingredients | % w/w |
|---|---|
| D.I. water | 67.5 |
| Xanthan gum [1] | 1.5 |
| Sodium Laureth Sulfate [2] (28%) | 25.0 |
| Decyl Glucocide [3] (50%) | 6.0 |
| Preservative | q.s |

[1] Fluid bed heat treated at 225° F. for 2.5 hr
[2] Standapol ES-2 (Henkel)
[3] Plantaren 2000 (Henkel)

This formula containing xanthan gum has good viscosity (12000 cps, Brookfield DV-I, spindle#6 @10 rpm), clarity, as well as short and smooth texture. Xanthan gum is used as a rheology modifier and a suspending agent. Air bubbles or encapsulation beads or glitters may be suspended due to the use of xanthan gum. In addition, it may also help to stabilize and enhance the foams as a foam stabilizer. A soft and smooth skin after feel is left after the use of this product.

Example 9

Anti-Dandruff Shampoo

| Ingredients | % w/w |
|---|---|
| D.I. water | 56.0 |
| Xanthan gum [1] | 1.0 |
| Disodium Cocoamphodiacetate [2] (50%) | 15.0 |
| Sodium Laureth Sulfate [3] (28%) | 25.0 |
| Zinc Pyrion NF (48%) | 2.0 |
| Citric acid (50%) | q.s. to pH = 6.5 |
| Preservative | q.s |

[1] Fluid bed heat treated at 225° F. for 2.5 hr
[2] Monateric CDX-38 (Henkel)
[3] Standapol ES-2 (Henkel)

This formula looks smooth and has a viscosity of 19430 cps (Brookfield, Helipath, Spindle T-B @10 rpm). No precipitation observed, indicating the suspending capability of xanthan gum. Xanthan gum helps to thicken the system and suspend the active.

Example 10

Anti-Acne Facial Gel

| Ingredients | % w/w |
|---|---|
| Part A | |
| Salicylic acid | 1.0 |
| Propylene glycol | 3.0 |
| Part B | |
| Xanthan gum [1] | 1.5 |
| D.I. water | 94.5. |
| NaOH solution (10%) | q.s. to pH ~4.0 |
| Preservative | q.s |

[1] Fluid bed heat treated at 225° F. for 2.5 hr

Xanthan gum forms a gel with smooth texture at low pH, and with the presence of salt. Xanthan gum is used as a good thickener/gel former, and imparts soft and smooth skin after feel. The films formed could leave the skin with a firm feel.

Example 11

Fragrance Gel with Xanthan Gum

| Ingredients | % w/w |
|---|---|
| Part A | |
| Xanthan gum [1] | 1.5 |
| D.I. water | 64.5 |
| Part B | |
| Ethanol, SDA-40 | 25.0 |
| PEG-40 Hydrogenated Castor Oil [2] | 5.0 |
| Fragrance | 4.0 |

[1] Fluid bed heat treated at 225° F. for 2.5 hr
[2] Cremophor RH 40 (BASF)

Xanthan gum is used as a thickener in a water and ethanol system. It can also serves as a fixative for the fragrance to provide a longer lasting effect due to the films formed by xanthan gum.

We claim:

1. A composition comprising:
   a heat-treated xanthan gum having a solution viscosity of about 15,000 cps or greater, in a 1% aqueous solution,
   wherein the xanthan gum has a solution viscosity of about 3000 cps or greater prior to heat treating and an ash content of about 8.5% or less,
   wherein the heat treated xanthan gum has a moisture content of about 8% or less, and
   wherein the heat treated xanthan gum exhibits a reduction in time to fully disperse the heat treated xanthan gum in water by at least 25% and no more than 70% compared to the xanthan gum prior to heat treatment.

2. The composition of claim 1, wherein the moisture content of the heat treated xanthan gum is about 1% or less.

3. The composition of claim 1, wherein the heat treated xanthan gum has clear to translucent clarity.

4. The composition of claim 1, wherein the heat treated xanthan gum exhibits an increase in solution viscosity in a 1% aqueous solution of about 10,000 cps or greater over the viscosity of the xanthan gum prior to heat treatment.

5. The composition of claim 1, wherein the heat treated xanthan gum is a modified heat treated xanthan gum and the modification is chosen from oxidation, enzyme conversion, acid hydrolysis, heat and/or acid dextrinization, shear, chemical modification, enzymatical modification, and physical modification.

6. The composition of claim 1, wherein the composition is a cosmetic or personal care composition.

7. The composition of claim 6, wherein the cosmetic or personal care composition is selected from the group consisting of a skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with alpha hydroxyl acid (AHA) and beta hydroxyl acid (BHA), and hair fixatives.

8. The composition of claim 7, wherein the cosmetic or personal care composition is a hair fixative and is selected from the group consisting of a hair sprays, gels, mousses, pomades, and waxes.

9. The composition of claim 1, wherein the composition is in the form of an emulsion, a gel, a liquid, a spray, a solid, a mousse, a powder, a wipe or a stick.

10. The composition of claim 1, wherein the heat treated xanthan gum is present in an amount from about 0.01 wt % to about 20 wt % of the composition.

* * * * *